United States Patent [19]
Fukusaki et al.

[11] Patent Number: 5,272,069
[45] Date of Patent: Dec. 21, 1993

[54] METHOD OF PRODUCING OPTICALLY ACTIVE HYDROXYESTERS

[75] Inventors: Eiichiro Fukusaki; Shuji Senda; Yutaka Nakazono; Tetsuo Omata; Ken Hibino, all of Osaka; Hiromichi Ota, Tokyo; Takeshi Sugai, Kawasaki, all of Japan

[73] Assignee: Nitto Denko Co. Ltd., Osaka, Japan

[21] Appl. No.: 634,914

[22] Filed: Dec. 27, 1990

[30] Foreign Application Priority Data

Dec. 27, 1989 [JP] Japan .................. 1-341578
Dec. 27, 1989 [JP] Japan .................. 1-341579
Mar. 13, 1990 [JP] Japan .................. 2-63665
Apr. 3, 1990 [JP] Japan .................. 2-89669

[51] Int. Cl.$^5$ ............................... C12P 7/40
[52] U.S. Cl. .................... 435/136; 435/134; 435/135; 435/280; 554/116; 554/121; 558/276; 560/183
[58] Field of Search .............. 435/135, 134, 136, 280; 554/115; 260/410.9, 405.5; 558/276

[56] References Cited

PUBLICATIONS

Lazar et al., "Synth. of Esters by Lipases", *Proceedings—World Conf. of Emerging Tech. Fats & Oils*, Baldwin ed., 1985, pp. 346–354.

*Primary Examiner*—Ronald W. Griffin
*Assistant Examiner*—Pamela S. Webber
*Attorney, Agent, or Firm*—Armstrong, Westerman, Hattori, McLeland, & Naughton

[57] ABSTRACT

This invention relates to methods for producing optically active hydroxyesters and also to methods for producing and purifying optically active five-membered ring lactones.

More specifically, the invention provides methods for efficiently, safely, and selectively producing and purifying optically active (R)-hydroxyester (shown by formula 1) and optically active (S)-hydroxyester (shown by formula 2) in high state of purity at ordinary temperature.

The invention also relates to application of the interconvertible optically active (R)-five-membered ring lacton (shown by formula 5).

They are intermediates for synthesizing various medicines, agricultural chemicals, and biologically active substances, however especially useful for synthesizing pheromone of a noxious insect, *Popillia japonica* Newman.

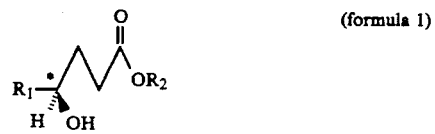

(formula 1)

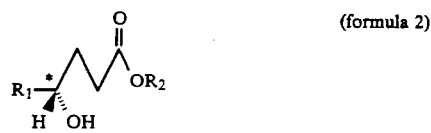

(formula 2)

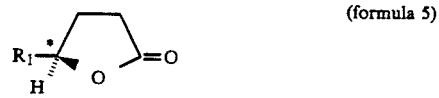

(formula 5)

(Here, $R_1$ denotes —C≡C—$R_3$ or —C=C—$R_3$; $R_2$ and $R_3$ denote straight chain or branched alkyl groups containing 1 to 10 carbon atoms; $R_4$ denotes alkyl groups, aralkyl groups, or haloalkyl groups containing 1 to 12 carbon atoms and the end group of $R_4$ may be carboxyl groups; * denotes asymmetricrbon atoms.)

3 Claims, No Drawings

METHOD OF PRODUCING OPTICALLY ACTIVE HYDROXYESTERS

INDUSTRIAL FIELD OF INVENTION

This invention relates to methods for producing optically active hydroxyesters and also to methods for producing and purifying optically active five-membered ring lactones.

More specifically, the invention provides methods for efficiently, safely, and selectively producing and purifying optically active substances in a high state of purity at ordinary temperatures.

The invention also relates to application of interconvertible optically active hydroxyesters and optically active five-membered ring lactones.

The hydroxyesters and lactones of the present invention are intermediates for synthesizing various medicines, agricultural chemicals, and biologically active substances and are especially useful for synthesizing a pheromone of a noxious insect, *Popillia japonica* Newman.

BACKGROUND OF THE INVENTION

Optically active hydroxyesters and five-membered ring lactones have been noted as important intermediates for synthesizing various medicines, agricultural chemicals, and biologically active substances.

Especially optically active (R)-4-hydroxy-tetradecynoates, one of (R)-4-hydroxyesters (formula 1), and optically active (R)-5-(1-decynyl)-oxacyclopentan-2-one, of (R)-five-membered ring lactones (formula 5), are important intermediates for synthesizing pheromone of *Popillia japonica* Newman (see Shuji Senda and Kenji Mori, Agrical. Biol. Chem., 47 (11) 2595 to 2598 (1983)).

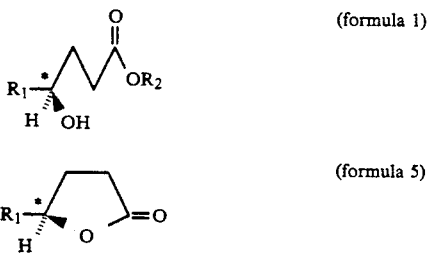

Here, $R_1$ denotes $-C\equiv C-R_3$ or $-C=C-R_3$; $R_2$ and $R_3$ denote straight chain or branched alkyl groups containing 1 to 10 carbon atoms; * denotes asymmetric carbon atoms.

Optically active (R)-4-hydroxyesters (formula 1) and optically active (R)-membered ring lactones (formula 5) are interconvertible.

Optically active (R)-4-hydroxyesters are lactonized to optically active (R)-five-membered ring lactones in the usual way.

On the other hand, optically active (R)-five-membered ring lactones are hydrolyzed and esterified to optically active (R)-4-hydroxyesters.

The activity of the pheromone of *Popillia jaonica* Newman, (R,Z)-(−)-5-(1-decenyl)-dihydro-2-(3H)-furanone, is drastically reduced in the presence of its (S,Z)-isomer.

It is said that existence of 0.5% (S,Z)-isomer lowers the activity of the pheromone to 60%, 2% (S,Z)-isomer to one third, and 6% (S,Z)-isomer to zero.

It is accordingly very important to produce, in a high state of purity, (R)-4-hydroxy-5-tetradecynoates and (R)-5-(1-decinyl)-oxacyclopentan-2-one.

However, no efficient producing and purifying process has been provided so far.

PRIOR ART

Production of optically active (R)-4-hydroxy-5-tetradecynoates ((R)-4-hydroxyesters) has been proposed.

The inventors have disclosed chemical and microbial synthesis of optically active (R)-4-hydroxy-5-tetradecynoates from 4-oxo-5-tetradecynoates (Japanese Published Unexamined Patent Applications No. Sho 59-157,055, and No. Hei 1-101,889, respectively).

Production of optically active (R)-five-membered ring lactones has also been disclosed; same are obtained by lactonzing optically active (R)-4-hydroxy-5-tetradecynoates.

PROBLEMS OF PRIOR ART

Although chemical synthesis (Japanese Published Unexamined Patent Application No. Sho 59-157,055) gives (R)-4-hydroxy-5-tetradecynoates in a high state of purity, it has some disadvantages and is thereby not practical.

The disadvantages are as follows:

(1) The method requires expensive asymmetric reducing agents;

(2) The temperature should be controlled to $-100°$ C.; and (3) The method requires expensive and dangerous reagents such as lithiun aluminum hydride.

The microbial synthesis (Japanese Published Unexamined Patent Application No. Hei 1-101,889) does not always give (R)-4-hydroxy-5-tetradecynoates in high yield and is thereby not practical.

Accordingly, the synthesis of optically active (R)-five-membered ring lactones from (R)-4-hydroxy-5-tetradecynoates does not promise high purity products and is not practical.

Furthermore, no practical methods have been proposed for purifying the reaction product, including (R)-five-membered ring lactones, of sufficient optical purity so as to obtain pure optically active (R)-five-membered ring lactone products.

DETAILED DESCRIPTION OF THE INVENTION

Hereinafter, the abovestated inventional embodiments are described in detail.

The inventors have created two methods (A), (B) for producing optically active hydroxyesters as a result of their study.

The characteristic method (A) for producing optically active hydroxyesters is the use of impure optically active hydroxyester, a mixture of optically active (R)-hydroxyester (shown by formula 1) and optically active (S)-hydroxyester (shown by formula 2).

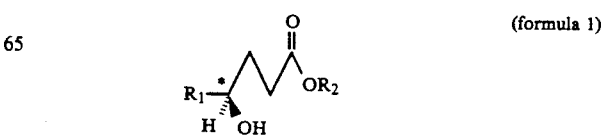

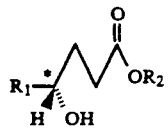

(formula 2)

Here, $R_1$ denotes $-C\equiv C-R_3$ or $-C=C-R_3$; $R_2$ and $R_3$ denote straight chain or branched alkyl groups containing 1 to 10 carbon atoms; * denotes asymmetric carbon atoms.

All mixtures containing optically active (R)-hydroxy ester (formula 1) and optically active (S)-hydroxyester (formula 2) are sufficient for use as a starting material. Therefore, for example, racemic hydroxyester (formula 6) is favorably used.

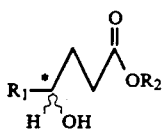

(formula 6)

Here, $R_1$ denotes $-C\equiv C-R_3$ or $-C=C-R_3$; $R_2$ and $R_3$ denote straight chain or branched alkyl groups containing 1 to 10 carbon atoms; * denotes asymmetric carbon atoms.

This racemic hydroxyester (formula 6) is easily produced.

4-hydroxy-5-tetradecynoie acid derivative synthesis is facilitated by dissolution of the starting material in a solvent, such as methanol, then reduction with sodium boron hydride, in a well known manner (Agric. Biol., 47(11), 2595–2598, 1983.

Examples of the racemic hydroxyester (formula 6) are selected from the group consisting of methyl 4-hydroxy-5-tetradecynoate, ethyl 4-hydroxy-5-tetradecynoate, ethyl 4-hydroxy-5-tetradecynoate, ethyl 4-hydroxy-5-tetradecenoate, methyl 4-hydroxy-5-tetradecenoate, methyl 4-hydroxy-5-tridecynoate, methyl 4-hydroxy-5-tetradodecynoate, etc.

Methyl 4-hydroxy-5-tetradecynoate is important as a intermediate for synthesizing the sex pheromone of Popillia Japonica Newman, a noxious insect for grass.

In this invention, the racemic hydroxyester (formula 6) is reacted with carboxylic acid or carboxylic anhydride in the presence of hydrolase in an organic solvent so as to acylate an optically active (R)-hydroxyester (formula 1) to produce the optically active (R)-diester (shown by formula 3) in a selective manner.

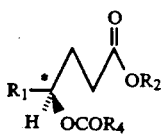

(formula 3.)

Here, $R_1$ denotes $-C\equiv C-R_3$ or $-C=C-R_3$; $R_2$ and $R_3$ denote straight chain or branched alkyl groups containing 1 to 10 carbon atoms; $R_4$ denotes alkyl groups, aralkyl groups, or haloalkyl groups containing 1 to 12 carbon atoms and the end group of $R_4$ may be carboxyl groups; * denotes asymmetric carbon atoms.

In this reaction, the enzyme to be used is a lipase such as a lipase derived from the pancreas of a pig, or from yeast, mold or bacteria.

Either purified or crude enzymes can be used, and the state of enzymes is not a restriction. Therefore same can be favorably used in any state (i.e. powder, grain, or dried biomass of microorganism containing the enzyme).

These enzymes can be used as is, or immobilized on a carrier

The organic solvent used in this reaction is a non-aqueous system solvents selected from the group consisting of hydrocarbon solvent like as n-hexane, n-heptane, n-octane, isobutane, isopentane, isooctane, and a cyclic hydrocarbon solvent like as cyclopentane, cyclohexane, and a halogenated hydrocarbon solvent like as dichloromethane, trichloromethane, and an aromatic hydrocarbon solvent like as benzene, toluene, xylene, and an ether group solvent like as diethylether, diisopropylether, n-butylether, tetrahydrofuran, tetrahydropyran and carbon tetrachloride etc.

Any carboxylic acid reactive with a monoester hydroxylated at the fourth carbon in the presence of a hydrolase may be used as the acylating agent in the process of the present invention, but carboxylic acids containing 2 to 10 carbon atoms are preferred. Examples of such carboxylic acids are acetic acid, propionic acid, butyric acid, valeric acid and capric acid.

Any carboxylic acid anhydride reactive with a monoester hydroxylated at the fourth carbon in the presence of a hydrolase may be used as the acylating agent in the process of the present invention, by anhydrides of acyclic carboxylic acids containing 2 to 10 carbons or of cyclic carboxylic acids containing 4 to 10atoms are preferred. Examples of such acyclic anhydrides are the anhydrides of acetic, propionic, butyric, valeric and capric acids. Examples of such cyclic anhydrides are succinic anhydride, maleic anhydride and glutaric anhydride.

The combination ratio of racemic hydroxyester (formula 6) and acyl group donater (a carboxylic acid or a carboxylic anhydride) is 1: not less than 0.5 in mole ratio, favorably.

The reaction temperature in this reaction is preferably within active temperature for the enzyme, in the range of 10° C. to 50° C.

After the asymmetric acylation reaction, the reaction mixture is separated into optically active (R)-diester (formula 3) and optically active (S)-hydroxyester (formula 2).

As for examples of this separating process, there are extraction by using organic solvent being slightly soluble in water, two solvents of insoluble organic solvent and water as two layers system, separation by using calomn, and distillation, etc.

The optically active (R)-diester (formula 3) obtained in the above manner can be easily converted into optically active (R)-hydroxyester (formula 1) as same purity as diester (formula 3) by hydrolyzing with alkali like pottasium hydroxide and other, and esterificating with cyanamide and others.

Another method (B) of producing optically active hydroxyesters is explained in detail below.

In this method of producing (B), the mixture of optically active (R)-diester (shown by formula 3) and optically active (S)-diester (shown by formula 4) is enough to use any proportion rate mixture as for example racemic diester (formula 7).

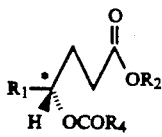
(formula 4)

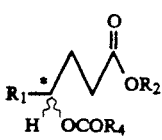
(formula 7)

Here, $R_1$ denotes —C≡C—R· or —C=C—$R_3$; $R_2$ and $R_3$ denote straight chain or branched alkyl groups containing 1 to 10 carbon atoms; $R_4$ denotes alkyl groups, aralkyl groups, or haloalkyl groups containing 1 to 12 carbon atoms and the end group of $R_4$ may be carboxyl groups; * denotes asymmetric carbon rbon atoms.

The racemic diester (formula 7) as a starting material in this method (B) is easily gained or produced.

For example, a synthesis manner of 4-butyloxy-5tetradecynoic acid derivaitive is illustrated; as one embodimed example of producing racemic diester (formula 7).

4-oxo-5-tetradecynoic acid derivative obtained by well known manner (Agric.Biol.47(11).2595~2598.1983) is reduced with sodium boron hydride, then acylated with carboxylic acid or carboxylic halogenide, thereafter racemic 4-hydroxy-5-tetradecynoic acid deriviative can be easily obtained.

The racemic diester (formula 7), using in this invention (B), is desired to be substrate for hydrolase, favorably having carbon number of $R_4$ group in the range of 1 to 10.

For example, $R_4$ is selected from the group consisting of methyl group, etyl group, propyl group, butyl group, baleryl group, caproyl group, isopropyl group, isobutyl group and others.

In this invention, the racemic diester (formula 7) is reacted with hydrolase in a solvent so as to asymmetrically hydrolyze the optically active (R)-diester (formula 3), and by adding, into this reaction solution, an acid to produce optically active (R)-hydroxyester (formula 2).

The solvents used in this reaction are either aqueous system or non-aqueous system solvents, without any restriction.

The examples of solvents are as follows:
(1) water or a buffer, such as a phosphoric acid buffer,
(2) non-aqueous system organic solvents; for example acyclic hydrocarbons solvents such as n-hexane, n-heptane, n-octane, isobutane, isopentane, isooctane; cyclic hydrocarbons solvents such as cyclopentane, cyclohexane; halogenized hydrocarbon solvents such as dichloromethane, trichloromethane, and carbon tetrachloride; aromatic hydrocarbon solvents such as benzene, toluene, xylene and ether group solvents such as diethylether, diisopropylether, n-butylether, tetrahydrofuran, tetrahydropyran,
(3) the above organic solvents saturated with water or buffer,
(4) two layer system solvents which consist of the above organic solvents and either water or buffer, In this reaction, the enzyme to be used is the same enzyme as used in the method of producing (A).

The reaction temperature is at the active temperature range for the enzyme employed, and ordinarily a range of about 10° C. to 50° C.

After asymmetric hydrolysis, an acid, such as hydrochloride, sulfonic acid or acetate is added to the reaction mixture until it becomes about pH 4, so as to produced optically active (R)-hydroxyester.

Thereafter, the thus obtained optically active (R)-hydroxyester (formula 1) is separated from the optically active (S)-diester (formula 4).

This separation process is the same as that shown in the method (A) of producing (R)-hydroxyester.

Moreover, the obtained optically active (S)-diester (formula 4) can be easily converted into optically active (S)-hydroxyester (formula 2) by hydrolyzing with alkali, and esterifying by the same manner as method (A) of producing optically active (R)-hydroxyester (formula 1), converted from (R)-diester (formula 3).

The relationship of the above-mentioned methods (A) and (B) is that optically active (R)-diester (formula 3), obtained in the method (A), can be used as a starting material in the method (B).

Therefore, the purification of optically active hydroxyester is possible by combination of the methods of producing (A) and (B).

Methyl 4-hydroxy-5-tetradecynoate is important as a intermediate for synthesizing the sex pheromone of *Popillia japonica* Newman, a noxious insect for grass, in the embodiment substances of optically active hydroxyesters obtained by the methods of producing (A) and (B).

(see Shuji Senda and Kenji Mori, Agrical. Biol. Chem., 47 (11) 2595 to 2598 (1983)).

The following are methods of producing and purifying optically active five-membered ring lactones.

The inventors created two producing methods and two purifying methods for optically active five-membered ring lactones (that are a method (C) for producing and a method (c) for purifying, a method (D) for producing and a method (d) for purifying).

The method (C) for producing optically active five-membered ring lactones used optically active hydroxyesters such as a mixture of optically active (R)-hydroxyester (shown by formula 1) and optically active (S)-hydroxyester (shown by formula 2), therefore, for example, racemic hydroxyester (formula 6) is favorably employed.

The racemic hydroxyester (formula 6) is a material easily gained or produced (explained in method (A), for producing optically active hydroxyesters).

The racemic hydroxyester (formula 6) is reacted with hydrolase in an organic solvent so as to selectively lactonize the (R)-optically active hydroxyester (formula 1) to the optically active (R)-five-membered ring lactone (shown by formula 5).

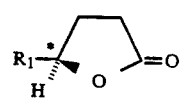
(formula 5)

Here, $R_1$ denotes —C≡C—$R_3$ or —C=C—$R_3$; $R_3$ denote straight chain or branched alkyl groups containing 1 to 10 carbon atoms; * denotes asymmetric carbon atoms.

In this reaction, the enzyme and the organic solvent are as the same as the enzyme and the organic solvent used in the method (A).

The reaction temperature is in the range of the active temperature for the enzyme, from 10° C. to 50° C.

After this asymmetric acylation, optically active (R)-five-membered ring lactone (formula 5) is separated from optically active (S)-hydroxyester (formula 2).

This separation is the same as in the method (A) for producing (R)-hydroxyesters, i.e. extraction by using an organic solvent which is slightly soluble in water (a two layer solvent system consisting of insoluble organic solvent and water). The separation is conducted by using a column, distillation, etc.

In the case of the impure (R)-five-membered ring lactone (formula 5) reaction product containing obtained through operations in the method (C) for producing, the following method (c) of purifying is useful.

First, the reaction product containing (R)-five-membered ring lactone (formula 5) obtained by the above method (c) is hydrolyzed so as to cleave the five-membered ring.

An alkali, favorably used in this reaction, is potassium hydroxide, sodium hydroxide, carbonic sodium, etc.

Further, the cleavage product is esterified so as to produce hydroxyester.

In this esterification, the divalent alcohol group shown by ROH (R denotes alkyl groups.) is ethanol, methanol etc., or diazo compounds such as diazomethane, diazoethane, and dimethyl uric acid.

Also catalysts such as cyanamid, hydrochloride acid, sulfuric acid, tosyl acid, pyridinum, or paratoluensulfonate etc. may be used in the reaction.

Moreover, in the case of using a tertiary amine such as triethylamine (in the above ROH), the tertiary amine reacts to cleave and esterify (i.e. hydrolyzing and catalyzing).

The obtained ester is treated in the same manner as shown in method (C) for producing (that is reacted with hydrolase in an organic solvent so as to lactonize the (R)-optically active hydroxyester (formula 1) to optically active (R)-five-membered ring lactone (shown by formula 5) selectively).

The obtained (R)-five-membered ring lactone (formula 5), obtained in the above manner, is highly purified.

In the case repeating the above method (c) for further purification same results in products having a higher state of purity.

(R)-five-membered ring lactone (formula 5) obtained by using the racemic hydroxyester (formula 6) as starting material is contained a small amounts with racemic hydroxyester (formula 6) as impurities. Therefore, it (the solution of formula 6) needs to purifying by the above method (c), for purifying, so as to obtain the substance in more high state of purity.

The purifying process of the method (c), for obtaining ring lactone, is accomplished as repeated as it can be obtained in the state of 100% ee. of (R)-five-membered ring lactone (formula 5).

The following explains another method (D) for producing (R)-five-membered ring lactone (formula 5).

The mixture of optically active (R)-diester (shown by formula 3) and optically active (S)-diester (shown by formula 4) is enough to use any proportion rate of optically active (R)-diester (formula 3) and optically active (S)-diester (formula 4). For example, racemic diester (formula 7) is favorably used.

The racemic diester (formula 7), as a starting material in the method (D), is easily gained or produced as explained as in the method (B).

The racemic diester (formula 7) is reacted with hydrolase in an organic solvent so as to lactonize the (R)-optically active hydroxyester (formula 1) to optically active (R)-five-membered ring lactone (shown by formula 5) selectively.

In this reaction, the enzyme and the organic solvent to be used are as same as the enzyme and the organic solvent used in the method (B) of producing. Also, the reaction temperature in this reaction is as same as the temperature in the method (B) of producing.

After the asymmetric lactonization, the thus obtained optically active (R)-five-membered ring lactone (formula 5) is separated from optically active (S)-diester (formula 4).

The separation manner is the same manner as in the method (A) of producing (R)-hydroxyesters.

In the case of the reaction product containing impurities (by obtaining through series of operations in the method (D) i.e. optically active (R)-five-membered ring lactone (formula 5), the following methods (d) of purifying are useful.

At first, (R)-five-membered ring lactone (formula 5) of method (D) of producing is hydrolyzed, cleavaged and esterified in the same manner as the method (c) of purifying.

The obtained esterificated hydroxyester product is acylated at the hydroxyl group to diester compound.

In the acylation, the carboxylic acid groups and a solvent used, in the above method (A) of producing, are favorably used.

The obtained diester compound is reacted with hydrolase in an organic solvent so as to lactonize optically active (R)-hydroxyester (formula 1) to optically active (R)-five-membered ring lactone (formula 5), again selectively, in the same manner as the method (D) of producing.

Optically active (R)-five-membered ring lactone (formula 5) by the above manner is in high state of purity by this purifying.

The above method (d) for purifying on (R)-five-membered ring lactone is repeated, as said product can be obtained in a higher state of purity.

(R)-five-membered ring lactone (formula 5) obtained by using racemic diester (formula 7) as a starting material, is contained small amounts of racemic diester (formula 7) as impurities. Therefore, requiring purification by the above method (c) for purifying, so as to be in the state of 100% ee. purity of (R)-five-membered ring lactone (formula 5).

Especially (R)-5-(1-decynyl)-oxacyclopentan-2-one, one of (R)-five-membered ring lactone obtained by the method (C) and (D) for producing and the method (c) and (d) for purifying are important intermediates for synthesizing pheromone (R,Z)-(−)-5-(1-decenyl)-dihydro-2-(3H)-furanone of a noxious insect, *Popillia japonica* Newman. (see Shuji Senda and Kenji Mori, Agrical. Biol. Chem., 47 (11) 2595 to 2598 (1983)).

Moreover it is clear that the starting material is the optically active (R)-hydroxyester (formula 1) obtained by the method (A) for producing as for the method (c) and the optically active (R)-diester (formula 3) obtained by the method (B) for producing as for the method (D), it can be obtained in more high state of purity of (R)-five-membered ring lactone (formula 5).

Also it is clear that optically active (R)-five-membered ring lactone (formula 5) is converted into optically active (R)-hydroxyester (formula 1) or the optically active (R)-diester (formula 3) by the method (c) or (d) for purifying.

Therefore it is possible to obtain the optically active hydroxyester and optically active five-membered ring lactone in a high state of purity by any combination of method (A) or (B) for producing the optically active hydroxyester and the method (C) or (D) for producing optically active five-membered ring lactone and the method (c) or (d) for purifying optically active five-membered ring lactone.

Hereinafter, the detailed Examples are described, as the effect of this Invention can be seen.

EXAMPLE 1

Toluene (50 ml), racemic methyl 4-hydroxy-5-tetradecynoate (500 mg), and n-butylic acid (300 mg) were poured into a 100 ml Erlenmeyer flask.

In the solution, lipase (500 mg) [trade name:Amano-P, maker:Amano Pharmacy] was added, and stirred to react for 16 hours by magnetic stirrer at 25° C.

The reaction mixture was filtrated, then the solvent in the obtained filtrate was removed by using a rotary evaporater, thereafter it was concentrated.

The oily substance obtained by the above manner was separated by silica gel chromatograghy (hexane/ethyl acetate) and identified as methyl (S)-4-hydroxy-5-tetradecynoate (yield amount of product; 300 mg, optical purity; 60% ee.) and methyl (R)-4-butyloxy-5-tetradecynoate (yield amount of product; 230 mg, optical purity; 94% ee.).

The optical purity was measured with NMR under Eu(tfc₃). Note; The optical purity in other Examples were measured in the same manner as Example 1.

EXAMPLE 2

Toluene (50 ml), racemic methyl 4-hydroxy-5-tetradecynoate (500 mg), and n-capronic acid (300 mg) were poured into a 100 ml Erlenmeyer flask.

In the solution, lipase (500 mg) [trade name:Amano-P, maker:Amano Pharmacy] was added, and stirred to react for 16 hours by magnetic stirrer at 25° C.

The reaction mixture was filtrated, then the solvent in the obtained filtrate was removed by using a rotary evaporater; thereafter it was concentrated.

The oily substance obtained by the above manner was separated by silica gel chromatography (hexane/ethyl acetate) and identified as methyl (S)-4-hydroxy-5-tetradecynoate (yield amount of product; 320 mg, optical purity; 50% ee.) and methyl (R)-4-caproxy-5-tetradecynoate (yield amount of product; 200 mg, optical purity; 90% ee.).

EXAMPLE 3

Toluene (50 ml), racemic methyl 4-hydroxy-5-tetradecynoate (500 mg), and acetic anhydride (300 mg) were poured into a 100 ml Erlenmeyer flask.

In the solution, lipase (500 mg) [trade name:Amano-P, maker:Amano Pharmacy] was added, and stirred to react for 14 hours by magnetic stirrer at 25° C.

The reaction mixture was filtrated, then the solvent in the obtained filtrate was removed by using a rotary evaporater; thereafter it was concentrated.

The oily substance obtained by the above manner was separated by silica gel chromatography (hexane/ethyl acetate) and identified as methyl (S)-4-hydroxy-5-tetradecynoate (yield amount of product; 330 mg, optical purity; 40% ee.) and methyl (R)-4-acetoxy-5-tetradecynoate (yield amount of product; 200 mg, optical purity; 75% ee.).

EXAMPLE 4

Toluene (50 ml), racemic metyl 4-hydroxy-5-tetradecynoate (500 mg), and butyric anhydride (400 mg) were poured into a 100 ml Erlenmeyer flask.

In the solution, lipase (500 mg) [trade name:Amano-P, maker:Amano Pharmacy] was added, and stirred to react for 14 hours by magnetic stirrer at 25° C.

The reaction mixture was filtrated, then the solvent in the obtained filtrate was removed by using a rotary evaporater; thereafter it was concentrated.

The oily substance obtained by the above manner was separated by silica gel chromatography (hexane/ethyl acetate) and identified as methyl (S)-4-hydroxy-5-tetradecynoate (yield amount of product; 360 mg, optical purity; 38% ee.) and methyl (R)-4-butyloxy-5-tetradecynoate (yield amount of product; 190 mg, optical purity; 90% ee.).

EXAMPLE 5

Toluene (50 ml), racemic methyl 4-hydroxy-5-tetradecynoate (500 mg), and succinic anhydride (500 mg) were poured into a 100 ml Erlenmeyer flask.

In the solution, lipase (500 mg) [trade name:Amano-P, maker:Amano Pharmacy] was added, and stirred to react for 14 hours by magnetic stirrer at 25° C.

The reaction mixture was filtrated, then the solvent in the obtained filtrate was removed by using a rotary evaporater; thereafter it was concentrated.

The oily substance obtained by the above manner was separated by silica gel chromatography (hexane/ethyl acetate) and identified as methyl (S)-4-hydroxy-5-tetradecynoate (yield amount of product; 250 mg, optical purity; 70% ee.) and half-ester of succinic acid and 4-position hydroxy group of methyl (R)-4-hydroxy-5-tetradecynoate (yield amount of product; 280 mg, optical purity; 94% ee.).

EXAMPLE 6

50 mM of phosphoric acid buffer (50 ml, pH7), and racemic methyl 4-butyloxy-5-tetradecynoate (500 mg) were poured into a 100 ml Erlenmeyer flask.

In the solution, lipase (0.5 ml) which was derived from *Aspergillus niger* [trade name:Paratase-A, maker:-Novo Ltd.] was added, and stirred to react for 16 hours by magnetic stirrer at 25° C.

In the reaction solvent, hydrochloric acid (2N) was added until the solvent reached pH 4, and it was extracted with diethyl ether, then the obtained extractive layer, from which the diethyl ether was removed by using a rotary evaporater, was concentrated.

The oily substance obtained by the above manner was separated by silica gel chromatography (hexane/ethyl acetate) and identified as methyl (R)-4-hydroxy-5-tetradecynoic acid (yield amount of product; 200 mg, optical purity; 60% ee.) and methyl (S)-4-butyloxy-5-tetradecynoate (yield amount of product; 230 mg, optical purity; 90% ee.).

EXAMPLE 7

50 mM of phosphoric acid buffer (50 ml, pH7), and racemic methyl 4-propyoxy-5-tetradecynoate (500 mg) were poured into a 100 ml Erlenmeyer flask.

In the solution, lipase (0.5 ml) which was derived from *Aspergillus niger* [trade name: Paratase-A, maker:- Novo Ltd.] was added, and stirred to react for 16 hours by magnetic stirrer at 25° C.

In the reaction solvent, hydrochloric acid(2N) was added until the solvent reached of pH 4, and it was extracted with diethyl ether, then the obtained extractive layer from which the diethyl ether was removed by using a rotary evaporater, thereafter it was concentrated.

The oily substance obtained by the above manner was separated by silica gel chromatography (hexane/ethyl acetate) to be methyl (R)-4-hydroxy-5-tetradecynoate (yield amount of product; 190 mg, optical purity; 50% ee.) and methyl (S)-4-propyoxy-5-tetradecynoate (yield amount of product; 230 mg, optical purity; 70% ee.).

EXAMPLE 8

50 mM of phosphoric acid buffer (50 ml, pH7), and racemic methyl 4-caproxy-5-tetradecynoate (500 mg) were poured into a 100 ml Erlenmeyer flask.

In the solution, lipase (0.5 ml) which was derived from *Aspergillus niger* [trade name:Paratase-A, maker:- Novo Ltd.] was added, and stirred to react for 16 hours by magnetic stirrer at 25° C.

In the reaction solvent, hydrochloric acid(2N) was added until the solvent reached pH 4, and it was extracted with diethyl ether, then the obtained extractive layer, from which the diethyl ether was removed by using a rotary evaporater, was concentrated.

The obtained oily substance in the above manner was separated by silica gel chromatography (hexane/ethyl acetate) to give methyl (R)-4-hydroxy-5-tetradecynoate (yield amount of product; 180 mg, optical purity; 58% ee.) and methyl (S)-4-caproxy-5-tetradecynoate (yield amount of product; 260 mg, optical purity; 70% ee.).

EXAMPLE 9

Water saturated butane (50 ml), and racemic methyl 4-butyloxy-5-tetradecynoate (500 mg) were poured into a 100 ml Erlenmeyer flask.

In the solution, lipase (0.5 ml) which was derived from *Aspergillus niger* [trade name:Paratase-A, maker:- Novo Ltd.] was added, and stirred to react for 16 hours by magnetic stirrer at 25° C.

In the reaction solvent, hydrochloric acid(2N) was added until the solvent reached of pH 4, and it was extracted with diethyl ether, then the obtained extractive layer, from which the diethyl ether was removed by using a rotary evaporater, was concentrated.

The oily substance obtained from the above manner was separated by silica gel chromatography (hexane/ethyl acetate) and identified as methyl (R)-4-hydroxy-5-tetradecynoate (yield amount of product; 180 mg, optical purity; 62% ee.) and methyl (S)-4-butyloxy-5-tetradecynoate (yield amount of product; 280 mg, optical purity; 70% ee.).

EXAMPLE 10

50 mM of phosphoric acid buffer (50 ml, pH7), and racemic methyl 4-butyloxy-5-tetradecynoate (500 mg) were poured into a 100 ml Erlenmeyer flask.

In the solution, lipase (500 mg) [trade name: Amano-P, maker:Amano Pharmacy] was added, and stirred to react for 16 hours by magnetic stirrer at 25° C.

In the reaction solvent, hydrochloric acid(2N) was added until the solvent reached pH 4, and it was extracted with diethyl ether, then the obtained extractive layer, from which the diethyl ether was removed by using a rotary evaporater, was concentrated.

The obtained oily substance in the above manner was separated by silica gel chromatography (hexane/ethyl acetate) to be methyl (R)-4-hydroxy-5-tetradecynoate (yield amount of product; 190 mg, optical purity; 50% ee.) and methyl (S)-4-butyloxy-5-tetradecynoate (yield amount of product; 250 mg, optical purity; 80% ee.).

EXAMPLE 11

Racemic methyl 4-hydroxy-5-tetradecynoate (3.39 g) was solved in diethyl ether (340 ml), in which lipase derived from pig pancreas (17 g) [trade name:PPL Type 2 L3126, maker:Sigma Ltd] was added, thereafter stirred to react for 48 hours at room temperature.

The reaction mixture was filtrated, then the residue was washed with ether.

The mixture of filtrate and washing was concentrated under reduced pressure, and the concentrated substance was separated by silica gel chromatography (silica gel:300 g, tetrachloromethane/ether 20:1) to be methyl (S)-4-hydroxy-5-tetradecynoate (yield amount of product; 1.74 g,) and (R)-5-(1-decynyl)-oxocyclopentane-2-one (yield amount of product; 1.27 g, optical purity; 80% ee.).

EXAMPLE 12

(R)-5-(1-decynyl)-oxocyclopentane-2-one (yield amount of product; 1.27 g, optical purity; 80% ee.) obtained at Example 11 was dissolved in methanol (100 ml), and triethylamine (5.9 ml) was added in the solution, thereafter the mixture was heated and refluxed to react for 2 hours.

After cooling, an acidic cation exchange resin (10 g) [trade name:Amberlist 15] was added in the reacted mixture, then it was stirred to neutralize.

The cation exchange resin was filtered under reduced pressure with a cotton plug, then removed by filtrating with filter paper (No. 5), there after the filtrate was concentrated under reduced pressure.

Toluene was added in the concentrated substance, then it was purified by silica gel chromatography (silica gel:100 g, tetrachloromethane/ether 20:1) to be methyl (R)-4-hydroxy-5-tetradecynoate (yield amount of product; 1.25 g, optical purity; 80% ee.)

EXAMPLE 13

Methyl (R)-4-hydroxy-5-tetradecynoate (yield amount of product; 1.25 g, optical purity; 80% ee.) obtained at Example 12 was solved in diethyl ether (125 ml), in which lipase derived from pig pancreas (7.25 g) [trade name:PPL Type 2 L3126, maker:Sigma Ltd] was added, thereafter stirred to react for 65 hours at room temperature.

The reaction mixture was filtrated, then the residue was washed with ether.

The mixture of filtrate and washing was concentrated under reduced pressure, and the concentrated substance was separated by silica gel chromatography (silica gel:300 g, tetrachloromethane/ether 20:1) to be methyl (S)-4-hydroxy-5-tetradecynoate (yield amount of product; 278 mg,) and (R)-5-(1-decynyl)oxocyclopentane-2-one (yield amount of product; 706 mg, optical purity; 98% ee.).

EXAMPLE 14

(R)-5-(1-decynyl)-oxocyclopentane-2-one (yield amount of product; 706 mg, optical purity; 98% ee.)

obtained at Example 13 was dissolved in methanol (100 ml), and triethylamine (3 ml) and added to the solution, thereafter the mixture was heating refluxed to react for 2 hours.

After cooling, a acidic cation exchange resin (5 g) [trade name:Amberlist 15] was added in the reacted mixture, then it was stirred to neutralize.

The cation exchange resin was filtrated under reduced pressure with a cotton plug continuously and the cation exchange resin was removed by filtrating with filter paper (No. 5); thereafter the filtrate was concentrated under reduced pressure.

Toluene was added to the concentrated substance, then purified by silica gel chromatography (silica gel:100 g, tetrachloromethane/ether 20:1) to be methyl (R)-4-hydroxy-5-tetradecynoate (yield amount of product; 690 mg, optical purity; 98% ee.)

EXAMPLE 15

Racemic methyl 4-succinyloxy-5-tetradecynoate (500 mg) was dissolved in a solution of hexane and water (1:1) (50 ml), in which lipase derived from yeast (0.5 g) [trade name: Lipase OF, maker:Meito Industry Ltd.] was added, thereafter stirred to react for 15 hours at room temperature.

The reaction mixture was filtrated, then residue was washed with ether.

The mixture of filtrate and wash was concentrated under reduced pressure, and the concentrated substance was separated by silica gel chromatography (silica gel:15 g, hexane/ethyl acetate 9:1) to be methyl (S)-4-succinyloxy-5-tetradecynoate (yield amount of product; 220 mg,) and (R)-5-(1-decynyl)-oxocyclopentane-2-one (yield amount of product; 180 mg, optical purity; 80% ee.).

EXAMPLE 16

Racemic methyl 4-butyloxy-5-tetradecynoate (500 mg) was dissolved in a solution of hexane and water (1:1) (50 ml), in which lipase derived from Pseudomonas (1 g) [trade name:Amano-P, maker:Amano Pharmacy] was added, thereafter stirred to react for 15 hours at room temperature.

The reaction mixture was filtrated, then the residue was washed with ether.

The mixture of filtrate and wash was concentrated under reduced pressure, and the concentrated substance was separated by silica gel chromatography (silica gel:15 g, hexane/ethyl acetate 9:1) to be metyl (S)-4-succinyloxy-5-tetradecynoate (yield amount of product; 240 mg) and (R)-5-(1-decynyl)-oxocyclopentane-2-one (yield amount of product; 150 mg, optical purity; 60% ee.).

EXAMPLE 17

(R)-5-(1-decynyl)-oxocyclopentane-2-one (yield amount of product; 180 mg, optical purity; 80% ee.) obtained by Example 15 was solved in methanol (15 ml), and triethylamine (0.6 ml) was added in the solution, thereafter the mixture was heated and refluxed to react for 2 hours.

After cooling, an acidic cation exchange resin (1 g) [trade name: Amberlist 15] was added in the reacted mixture, then stirred to neutralize.

The cation exchange resin was filtrated under reduced pressure with a cotton plug continuously, the cation exchange resin was removed by filtrating with filter paper (No. 5), thereafter the filtrate was was concentrated under reduced pressure.

Toluene was added in the concentrated substance, then it was purified by silica gel chromatography (silica gel: 10 g, tetrachloromethane/ether 20:1) to be methyl (R)-4-hydroxy-5-tetradecynoate (yield amount of product; 160 mg, optical purity; 80% ee.)

EXAMPLE 18

Methyl (R)-4-hydroxy-5-tetradecynoate (amount of product; 100 mg, optical purity; 80% ee.) obtained at Example 17 was solved in pyridine (150 ml), and succinic anhydride (50 mg) was added in the solution, thereafter the mixture was heating refluxed to react for 16 hours.

The reaction mixture was filtrated to obtain filtrate.

The filtrate was concentrated under reduced pressure, and the concentrated substance was purified by silica gel chromatography (silica gel: 2 g, hexane/ethyl acetate 9:1) to be methyl (R)-4-succinyloxy-5-tetradecynoate (yield amount of product; 110 mg, optical purity; 80% ee.)

The obtained metyl (R)-4-succinyloxy-5-tetradecynoate was dissolved in a solution of hexane and water (1:1) (50 ml), in which lipase derived from yeast (0.1 g) [trade name: Lipase OF, maker: Meito Industory Ltd.] was added, thereafter stirred to react for 15 hours at room temperature.

The reaction mixture was filtrated, then the residue was washed with ether.

The mixture of filtrate and wash was concentrated under reduced pressuer, and the concentrated substance was separated by silica gel chromatography (silica gel: 2 g, hexane/ethyl acetate 9:1) to be metyl (S)-4-succinyloxy-5-tetradecynoate (yield amount of product; 20 mg,) and (R)-5-(1-decynyl)oxocyclopentane-2-one (yield amount of product; 80 mg, optical purity; 99.8% ee.)

EFFECTS OF THE INVENTION

The inventional methods are methods to easily produce hydroxyesters and five-membered ring lactones in the state of obtained high purity of optical activity, efficiently and safely, said producing at ordinary temperature.

We claim:

1. A method of producing an optionally active (R)-diester of the formula

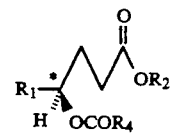

wherein $R_1$ is $-C{=}C{=}R_3$ or $-C{\equiv}C-R_3$; $R_2$ and $R_3$ are each straight chain or branched alkyl groups containing 1 to 10 carbon atoms; $R_4$ is an alkyl, alkylcarboxylic acid, haloalkyl, haloalkylcarboxylic acid, aralkyl or aralkylcarboxylic acid group containing 1 to 12 carbons; and * designates an asymmetric carbon atom; which comprises adding a carboxylic acid of the formula $R_4-COOH$ or an anhydride thereof having a formula selected from the group consisting of

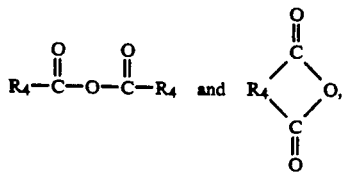 and 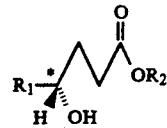

to an organic solvent solution of a mixture of a (R)-hydroxyester of the formula

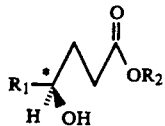

and an (S)-hydroxyester of the formula

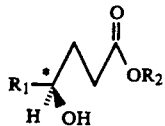

in the presence of a lipase to selectively acylate the (R)-hydroxyester to the (R)-diester; and separating said (S)-hydroxyester from said (R)-diester.

2. A method according to claim 1, wherein the lipase is derived from the pancreas of a pig, or from a yeast, mold or bacteria.

3. A method according to claim 1, wherein the (R)- and (S)-hydroxyesters are methyl 4-hydroxy-5-tetradecynoate.

* * * * *